United States Patent [19]
Iwasaki et al.

[11] Patent Number: 5,792,876
[45] Date of Patent: Aug. 11, 1998

[54] PROCESS FOR PRODUCING ACETALS

[75] Inventors: Hideharu Iwasaki; Masahiko Kitayama; Takashi Onishi. all of Hasaki-machi, Japan

[73] Assignee: Kuraray Co., Ltd., Kurashiki, Japan

[21] Appl. No.: 744,303

[22] Filed: Nov. 6, 1996

[30] Foreign Application Priority Data

Nov. 6, 1995 [JP] Japan ................ 7-311548
Nov. 20, 1995 [JP] Japan ................ 7-325003

[51] Int. Cl.$^6$ ............ C07C 321/00; C07C 31/18; C07C 63/34; C07C 69/76
[52] U.S. Cl. ............ 549/347; 544/352; 544/357; 544/367; 544/369; 544/430; 560/56; 560/57; 560/63; 560/64; 560/65; 560/81; 560/100; 560/102; 560/116; 560/118; 560/180; 560/182; 560/183; 560/184; 560/186; 560/187; 562/467; 562/473; 562/474; 562/475; 562/498; 562/508; 562/579; 562/580; 562/586; 562/587; 568/561; 568/542; 568/544; 568/715; 568/807; 568/808; 568/809; 568/811; 568/816; 568/822; 568/841; 568/852
[58] Field of Search ................ 568/852, 811, 568/561, 592, 596, 715, 807, 808, 809, 816, 822, 841; 544/352, 347, 367, 369, 357, 430; 560/56, 57, 63, 64, 65, 81, 100, 102, 110, 118, 180, 182, 183, 184, 186, 187; 562/467, 473, 474, 475, 498, 508, 579, 582, 586, 587

[56] References Cited

PUBLICATIONS

Chemical Abstracts, vol. 99, No. 7, pp. 503–504, Aug. 15, 1983, AN 53125 & JP–58–55440, Apr. 1, 1983.

Chemical Abstracts, vol. 90, No. 17, pp. 462–463, Apr. 23, 1979, AN 137263, JP–53–132514, Nov. 18, 1978.

Journal of the Chemistry Society, Chemical Communications, No. 22, pp. 976–977, Nov. 15, 1978, Jean–Louis Luche, et al., "Efficient Synthesis of Acetals Catalysed by Rare Earth Chlorides".

*Primary Examiner*—C. Warren Ivy
*Assistant Examiner*—Raymond Covington
*Attorney, Agent, or Firm*—Oblon, Spivak, McClelland, Maier & Neustadt, P.C.

[57] ABSTRACT

A process is described for producing acetals comprising reacting an aldehyde or a ketone with an alcohol in the presence of a titanium compound having an acetylacetone as a ligand, or in the presence of a compound selected from the group consisting of stannous chloride dihydrate, cerium chloride hexahydrate and bismuth chloride. The process can be used in the synthesis of unstable acetals or when water exists in the reaction mixture, and therefore the process can be used for a wide variety of applications.

20 Claims, No Drawings

PROCESS FOR PRODUCING ACETALS

BACKGROUND OF THE INVENTION

1. Field of the Invention

This invention relates to a process for producing acetals. The acetals obtained by the process provided by the present invention are useful as starting materials for perfumes, agricultural chemicals, pharmaceuticals or the like.

2. Description of the Related Art

A number of processes have been reported as processes for producing acetals by the reaction of an aldehyde or ketone and an alcohol. For example, the following processes described in (1) to (5) are known.

(1) A process in which p-toluenesulfonic acid is used as a catalyst (see "Org. Synth. Coll. Vol. V, 303(1973)").

(2) A process in which pyridinium p-toluenesulfonate is used as a catalyst (see "Synthesis, 724(1979)").

(3) A process in which an acid-type ion-exchange resin is used as a catalyst (see "J. Chem. Soc. Perkin Trans I, 158(1979)").

(4) A process in which aluminum chloride is used as a catalyst (see "Synthesis, 711(1989)").

(5) A process in which an alumina is used as a catalyst (see "Tetrahedron Lett., 4764(1985)").

In each of the above-described processes (1)–(4) for producing acetals, however, the acidic catalyst employed is strongly acidic so that when the process is applied to the synthesis of an unstable acetal such as an acetal formed from an enal or enone, or an acetal formed from allyl alcohol, a dealcoholytic reaction or a dehydration reaction proceeds as a side reaction and the desired acetal cannot be obtained in a high yield.

In addition, the above-described process (4) or (5) for producing acetals is accompanied with the problem that when an alcohol having a high water content is used or when removal of water content from the reaction system cannot be effected sufficiently, the catalyst is deactivated and the reaction does not proceed.

SUMMARY OF THE INVENTION

An object of the present invention is therefore to provide a process for producing acetals which process can also be applied to the synthesis of unstable acetals or when water exists in the reaction system, and thus the process can be used for a wide variety of applications.

The object of the invention can be achieved by the invention described below.

The present invention provides a process for producing an acetal of the following formula (4) or (5):

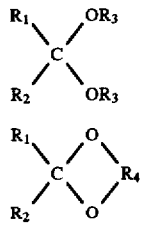

wherein $R_1$ and $R_2$ each independently represents a hydrogen atom or a monovalent hydrocarbon group with 1 to 20 carbon atoms which can have a substituent, or $R_1$ and $R_2$ are coupled together to form an alkylene group which can have an ethereal bond therein; $R_3$ represents a monovalent hydrocarbon group with 1 to 20 carbon atoms which can have a substituent; and $R_4$ represents an alkylene group which can have an ethereal bond therein, comprising reacting an aldehyde or a ketone represented by the following formula (1):

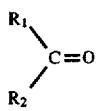

wherein $R_1$ and $R_2$ have the same meanings as defined above with an alcohol represented by the following formula (2) or (3):

wherein $R_3$ and $R_4$ have the same meanings as defined above, in the presence of a catalyst selected from the group consisting of stannous chloride dihydrate, cerium chloride hexahydrate and bismuth chloride, a titanium compound having acetylacetone as a ligand or a mixture thereof.

DETAILED DESCRIPTION OF THE INVENTION

The present invention is described in detail hereinbelow.

In the above formulas (1) to (5) which represent a ketone, an aldehyde and an alcohol which are starting materials, and an acetal which is the product, respectively, examples of the monovalent hydrocarbon group with 1 to 20 carbon atoms represented by $R_1$ or $R_2$ include but are not limited to alkyl groups such as methyl, ethyl, propyl, n-butyl, t-butyl, isoamyl and octyl; cycloalkyl groups such as cyclopentyl and cyclohexyl; alkenyl groups such as allyl, methallyl, crotyl and phenyl; alkynyl groups such as 2-propynyl; aryl groups such as phenyl, tolyl, xylyl and naphthyl; aralkyl groups such as benzyl and phenethyl; and a cinnamyl group.

Examples of the monovalent hydrocarbon group with 1 to 20 carbon atoms represented by $R_3$ include but are not limited to alkyl groups such as methyl, ethyl, propyl, n-butyl, t-butyl, isoamyl and octyl; cycloalkyl groups such as cyclopentyl and cyclohexyl; alkenyl groups such as allyl, methallyl, crotyl and phenyl; alkynyl groups such as 2-propynyl; aralkyl groups such as benzyl and phenethyl; and a cinnamyl group.

These hydrocarbon groups can be unsubstituted or substituted with any substituent which does not inhibit the acetalization reaction. Examples of the substituent include but are not limited to halogen atoms such as chlorine, bromine and iodine; carboxyl group; alkoxycarbonyl groups such as methoxycarbonyl and ethoxycarbonyl; and alkoxy groups such as methoxy and ethoxy.

When $R_1$ and $R_2$ are coupled together to form an alkylene group which can have an ethereal bond therein, examples of such an alkylene group include but are not limited to ethylene, propylene, tetramethylene and pentamethylene groups and a divalent group represented by the following formulas:

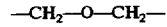

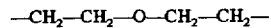

Preferred alkylene groups represented by $R_4$ having an ethereal bond therein are those exemplified above.

There is no particular limitation on the aldehyde or ketone which can be used in the method of the present invention. The aldehyde or ketone may contain a double bond, triple bond or aromatic ring.

Preferred aldehydes include but are not limited to formaldehyde, acetaldehyde, propionaldehyde, butyraldehyde, isobutyraldehyde, isovaleral, hexanal, octanal, methacrolein, crotonaldehyde, senecioaldehyde, citral, citronellal, benzaldehyde and cinnamaldehyde. Preferred ketones include but are not limited to methyl ethyl ketone, pinacolone, cyclohexanone, 2-octanone, mesityl oxide, 6-methyl-5-hepten-2-one, acetophenone and propiophenone.

Preferred alcohols which may be used in the method of the present invention include methanol, ethanol, propanol, butanol, allyl alcohol, methallyl alcohol, prenol, isoprenol, geraniol, nerol, benzyl alcohol, 2-phenylethanol, ethylene glycol, 1,2-propanediol, 1,4-butanediol and diethylene glycol. A primary alcohol is preferred when a faster reaction rate is desired.

There is no particular limitation on the amount of an alcohol used. To obtain an acetal in a high yield, however, the alcohol is generally used in an amount such that the hydroxyl group in the alcohol is at least 1 mole, preferably at least 2 moles, per mole of the carbonyl group in the aldehyde or ketone. There is no particular limitation on the upper limit of the amount of alcohol, but the amount of alcohol should be controlled to limit the production cost of acetals. The alcohol is generally used in an amount such that the hydroxyl group in the alcohol is at most 10 moles per mole of the carbonyl group in the aldehyde or ketone.

Commercially available stannous chloride dihydrate, cerium chloride hexahydrate and bismuth chloride can be used as a catalyst in the method of the present invention. These compounds can be used either singly or in combination.

Examples of the titanium compound having acetylacetone as a ligand, which compound is used as a catalyst in the present invention, include but are not limited to titanium acetylacetonate, titanium oxy acetylacetonate and titanium oxy acetylacetonate polymer. Commercially available titanium compounds can be used. These titanium compounds can be used either singly or in combination.

The amount of catalyst is chosen to be sufficient to allow the reaction to proceed, but not to lower the stability of the resulting acetal. In general, these catalysts are used in an amount such that their concentration may fall within a range of 0.1 ppm to 2%, preferably 1–500 ppm, relative to the reaction mixture.

The compounds chosen as catalysts in the method of the present invention are not strongly acidic. In addition, their catalytic activity is not decreased in the presence of water. The process of the present invention therefore makes it possible to produce an acetal in a high yield without causing a side reaction, even if applied to the synthesis of an unstable acetal such as an acetal formed from an enal or enone, or an acetal formed from allyl alcohol. The process of the present invention also makes it possible to prepare an acetal in a high yield even when water exists in the reaction system.

In the method of the present invention, a solvent is not required but it is possible to use a solvent when it does not inhibit the acetalization reaction. Preferred solvents include but are not limited to saturated aliphatic hydrocarbons such as hexane, heptane, octane and cyclohexane; aromatic hydrocarbons such as toluene and benzene; ethers such as diethyl ether and diisopropyl ether; and halogenated hydrocarbons such as methylene chloride and dichloroethane.

There is no particular limitation on the amount of the solvent. It is however preferred to use the solvent within a range which does not lower the volumetric efficiency of the reaction. Generally, the solvent is used in an amount within a range of 0.1 to 2 times the volume of the aldehyde or ketone.

The method of the present invention is preferably conducted in an inert gas atmosphere such as nitrogen or argon.

In the present invention, an aldehyde or a ketone, an alcohol, a catalyst such as stannous chloride dihydrate, cerium chloride hexahydrate or bismuth chloride, or a titanium compound having acetylacetone as a ligand, and optionally a solvent are mixed together and the resulting mixture is then reacted in a reaction vessel equipped with a stirrer at a predetermined reaction temperature.

It is also possible to add an alcohol in portions to the reaction vessel into which an aldehyde or a ketone and a catalyst have been charged in advance. In this case, the alcohol can be added as it is or in the form of solution in an appropriate solvent.

In the method of the present invention, water is formed as a byproduct as the reaction progresses. To obtain an acetal in a high yield, the water is preferably removed so as to prevent the hydrolysis of the acetal.

Known methods for removing water from the reaction mixture can be used, such as by azeotropic distillation or the use of a dehydrating agent, e.g., molecular sieves, anhydrous magnesium sulfate or anhydrous sodium sulfate.

For removing water from the reaction mixture by azeotropic distillation, a preferred method is one in which water is removed as an azeotropic mixture with the aldehyde or ketone which is the starting material. In this case, the water is preferably separated from the distillate using a water separator such as Dean-Stark water separator and then the water-removed distillate is returned to the reaction mixture.

In addition, water can be distilled off from the reaction mixture using a solvent, such as toluene, which can form an azeotropic mixture with water.

The process of the present invention is generally conducted at atmospheric pressure or under reduced pressure, more specifically, within a range of 15 mmHg to 760 mmHg, preferably 100 mmHg to 760 mmHg.

The reaction temperature, which is suitably set depending on the reaction pressure, generally falls within a range of −30° C. to 200° C. The lower the reaction temperature is, the higher the yield of the resulting acetal.

After the completion of the reaction, the acetal obtained can be isolated easily by separating it from unreacted aldehyde or ketone and unreacted alcohol by distilling the reaction mixture or like means.

The acetal thus obtained can be further purified by distillation, column chromatography or the like, if necessary.

Various aldehydes can be obtained according to the process provided by the present invention. Isovaleral dimethallyl acetal ($R_1$=an isobutyl group, $R_2$=a hydrogen atom and $R_3$=a methallyl group) is novel and can be used as a component of a perfume.

Other features of the present invention will become apparent in the course of the following descriptions of the exemplary embodiments which are given for illustration of the present invention and are not intended to be limiting thereof.

EXAMPLES

Example 1

In a 300 ml three-necked flask equipped with a water separator, 86 g (1 mole) of isovaleral, 148 g (2 moles) of methallyl alcohol and 2 mg of stannous chloride dihydrate were charged. The resulting mixture was heated at 85° C. under pressure of 180 mmHg for 10 hours in an argon atmosphere while removing the water formed from the reaction mixture by azeotropic distillation. When water was no longer distilled from the reaction, unreacted isovaleral and methallyl alcohol were distilled off under reduced pressure. Distillation of the residue under reduced pressure gave 195.5 g of isovaleral dimethallyl acetal [$R_1$=an isobutyl group, $R_2$=a hydrogen atom and $R_3$=a methallyl group] (boiling point: 125° C./25 mmHg) (yield: 90.5%). The properties of the product are shown below:

$^1$H-NMR [$CDCl_3$, δ (ppm)]: 0.93(d,6H,J=5.0Hz), 1.56(m, 3H), 1.76(s,6H), 3.80(d,2H,J=9.3Hz), 3.99(d,2H,J=9.3Hz), 4.68(t,1H,J=4.4Hz), 4.88(bs,2H), 4.99(bs,2H).

Example 2

In a 300-ml three-necked flask equipped with a water separator, 70 g (1 mole) of crotonaldehyde, 144 g (2 mole) of crotyl alcohol, 3 mg of stannous chloride dihydrate and 40 g of hexane were charged. The resulting mixture was heated at 70° C. under atmospheric pressure and for 4 hours in a nitrogen atmosphere while removing the water formed from the reaction mixture by azeotropic distillation. When water was no longer distilled, the solvent (hexane) and unreacted starting materials were distilled off under reduced pressure. Distillation of the residue under reduced pressure gave 182.2 g of crotonaldehyde dicrotyl acetal [$R_1$=a 1-propenyl group, $R_2$=a hydrogen atom and $R_3$=a crotyl group) (boiling point: 120° C./25 mmHg) (yield: 91.9%).

Example 3

In a 300-ml three-necked flask equipped with a water separator, 154 g (1 mole) of citronellal, 210 g (2.4 moles) of phenol and 3.6 mg of stannous chloride dihydrate were charged. The resulting mixture was heated at 120° C. under a pressure of 110 mmHg for 8 hours in a nitrogen atmosphere while removing the water formed from the reaction mixture by azeotropic distillation. When water was no longer distilled, unreacted starting materials were distilled off under reduced pressure. Purification of the residue by chromatography on a silica gel column gave 278.5 g of citronellal diprenyl acetal [$R_1$=a citronellyl group, $R_2$=a hydrogen atom and $R_3$=a phenyl group] (yield: 91.4%).

Example 4

In a 300-ml three-necked flask equipped with a water separator, 98 g (1 mole) of cyclohexanone, 148 g (2 moles) of n-butanol, 2.4 mg of stannous chloride dihydrate and 40 g of toluene were charged. The resulting mixture was heated at 125° C. under atmospheric pressure for 6 hours in a nitrogen atmosphere while removing the water formed from the reaction mixture by azeotropic distillation. When water was no longer distilled, the solvent (toluene) and unreacted starting materials were distilled off under reduced pressure. Distillation of the residue under reduced pressure gave 214.3 g of cyclohexanone dibutyl acetal [$R_1$, $R_2$=a pentamethylene group and $R_3$=a n-butyl group] (boiling point: 102° C./3 mmHg) (yield: 94.0%).

Example 5

In a 300-ml three-necked flask equipped with a water separator, 84 g (1 mole) of senecioaldehyde, 190 g (2.2 moles) of prenol and 2 mg of stannous chloride dihydrate were charged. The resulting mixture was heated at 100° C. under the pressure of 90 mmHg for 6 hours in an argon atmosphere while removing the water formed from the reaction mixture by azeotropic distillation. When water was no longer distilled, the solvent (hexane) and unreacted starting materials were distilled off under reduced pressure. Distillation of the residue under reduced pressure gave 223.3 g of senecioaldehyde diprenyl acetal ($R_1$=an isobutenyl group, $R_2$=a hydrogen atom and $R_3$=a prenyl group] (boiling point: 142° C./15 mmHg) (yield: 93.8%).

Example 6

In a 100-ml three-necked flask, 24 g (0.2 mole) of phenylacetaldehyde, 18 g (0.24 mole) of n-butanol, 10 g of anhydrous magnesium sulfate and 0.1 mg of stannous chloride dihydrate were charged. The resulting mixture was stirred at 100° C. under atmospheric pressure for 6 hours in a nitrogen atmosphere. After the removal of magnesium sulfate, the residue was purified by chromatography on a silica gel column to give 43.1 g of phenylacetaldehyde dibutyl acetal [$R_1$=a benzyl group, $R_2$=a hydrogen atom and $R_3$=an n-butyl group] (yield: 86.3%).

Example 7

In a 100-ml three-necked flask, 17.2 g (0.2 mole) of isovaleral, 23.2 g (0.21 mole) of benzyl alcohol, 10 g of anhydrous magnesium sulfate and 0.1 mg of stannous chloride dihydrate were charged. The resulting mixture was stirred at 15° C. under atmospheric pressure for 4 hours in a nitrogen atmosphere. After the removal of magnesium sulfate, the residue was purified by chromatography on a silica gel column to give 48.6 g of isovaleral dibenzyl acetal [$R_1$=an isobutyl group, $R_2$=a hydrogen atom and $R_3$=a benzyl group) (yield: 85.5%).

Example 8

In a 100-ml three-necked flask, 17.2 g (0.2 mole) of isovaleral, 12.4 g (0.2 mole) of ethylene glycol, 10 g of toluene, 12 g of anhydrous magnesium sulfate and 0.2 mg of stannous chloride dihydrate were charged. The resulting mixture was stirred at 0° C. under atmospheric pressure for 3 hours in a nitrogen atmosphere. After the removal of magnesium sulfate, the residue was purified by chromatography on a silica gel column to give 25.0 g of isovaleral ethylene glycol acetal [$R_1$=an isobutyl group , $R_2$=a hydrogen atom and $R_3$=an ethylene group] (yield: 96.3%).

Example 9

The general procedure of Example 2 was repeated except that 4 mg of cerium chloride hexahydrate was used instead of 3 mg of stannous chloride dihydrate to give 178.5 g of crotonaldehyde dicrotyl acetal (yield: 91.1%).

Example 10

The general procedure of Example 5 was repeated except that 3 mg of cerium chloride hexahydrate was used instead of 2 mg of stannous chloride dihydrate to give 210.1 g of senecioaldehyde diprenyl acetal (yield: 88.3%).

Example 11

In a 300-ml three-necked flask, 98 g (1 mole) of cyclohexanone, 148 g (2 moles) of n-butanol, 50 g of molecular sieve 4A, 2 mg of cerium chloride hexahydrate and 40 g of toluene were charged. The resulting mixture was stirred at 25° C. under atmospheric pressure for 12 hours in a nitrogen atmosphere. After the removal of the molecular sieve 4A, the solvent (toluene) and unreacted starting materials were distilled off under reduced pressure. Distillation of the residue under reduced pressure gave 212.2 g of cyclohexanone dibutyl acetal (yield: 93.1%).

Example 12

The general procedure of Example 8 was repeated except that 0.2 mg of cerium chloride hexahydrate was used instead of 0.2 mg of stannous chloride dihydrate to give 24.2 g of isovaleral ethylene glycol acetal (yield: 93.3%).

Example 13

The general procedure of Example 2 was repeated except that 72 g (1 mole) of n-butanal and 2 mg of bismuth chloride were used instead of 70 g of crotonaldehyde and 3 mg of stannous chloride dihydrate, respectively to give 177.0 g of n-butanal dicrotyl acetal ($R_1$=an n-propyl group, $R_2$=a hydrogen atom and $R_3$=a crotyl group] (boiling point: 116° C./25 mmHg) (yield: 89.4%).

Example 14

The general procedure of Example 5 was repeated except that 2-mg of bismuth chloride was used instead of 2 mg of stannous chloride dihydrate to give 210.0 g of senecioaldehyde diprenyl acetal (yield: 89.5%).

Example 15

The general procedure of Example 1 was repeated except that 2 mg of bismuth chloride was used instead of 2 mg of stannous chloride dihydrate to give 190.5 g of isovaleral dimethallyl acetal (yield: 88.2%).

Example 16

In a 300-ml three-necked flask, 98 g of cyclohexanone, 148 g of n-butanol, 50 g of anhydrous magnesium sulfate, 2 mg of bismuth chloride and 80 g of toluene were charged. The resulting mixture was stirred at 10° C. under atmospheric pressure for 10 hours in a nitrogen atmosphere. After magnesium sulfate was removed from the reaction mixture, the solvent (toluene) and unreacted starting materials were distilled off under reduced pressure. Distillation of the residue under reduced pressure gave 207.7 g of cyclohexanone dibutyl acetal (yield: 89.4%).

Example 17

The general procedure of Example 2 was repeated except that 3 mg of titanium acetylacetonate (product of Matsumoto Kosho Co., Ltd.) was used instead of 3 mg of stannous chloride dihydrate to give 189.5 g of crotonaldehyde dicrotyl acetal (boiling point: 120° C./25 mmHg) (yield: 95.2%).

Example 18

In a 300-ml three-necked flask, 72 g (1 mole) of n-butanal, 144 g of crotyl alcohol, 3 mg of titanium acetylacetonate, 80 g of molecular sieve 4A and 50 g of toluene were charged. The resulting mixture was stirred at 20° C. under atmospheric pressure for 12 hours in a nitrogen atmosphere. After the removal of the molecular sieve 4A from the reaction mixture, the solvent (toluene) and the unreacted starting materials were distilled off under reduced pressure. Distillation of the residue under reduced pressure gave 189.1 g of n-butanal dicrotyl acetal (boiling point: 116° C./25 mmHg) (yield: 95.5%).

Example 19

The general procedure of Example 4 was repeated except that 2 mg of titanium acetylacetonate was used instead of 2.4 mg of stannous chloride dihydrate to give 212.0 g of cyclohexanone dibutyl acetal (boiling point: 102° C./3 mmHg) (yield; 93.0%).

Example 20

The general procedure of Example 5 was repeated except that 2 mg of titanium acetylacetonate was used instead of 2 mg of stannous chloride dihydrate to give 229.2 g of senecioaldehyde diprenyl acetal (boiling point: 142° C./15 mmHg) (yield: 96.3%).

Example 21

The general procedure of Example 5 was repeated except that 2 mg of titanium oxy acetylacetonate (product of Dojin Kagaku Co., Ltd.) was used instead of 2 mg of stannous chloride dihydrate to give 227.3 g of senecioaldehyde diprenyl acetal (yield: 95.5%).

Example 22

The general procedure of Example 4 was repeated except that 1 mg of a titanium oxy acetylacetonate polymer (product of Matsumoto Kosho Co., Ltd.) was used instead of 2.4 mg of stannous chloride dihydrate to give 210.2 g of cyclohexanone dibutyl acetal (yield: 92.2%).

Example 23

The general procedure of Example 1 was repeated except that 2 mg of titanium oxy acetylacetonate was used instead of 2 mg of stannous chloride dihydrate to give 149.7 g of isovaleral dimethallyl acetal (yield: 69.3%).

Example 24

The general procedure of Example 1 was repeated except that 2 mg of titanium oxy acetylacetonate was used instead of 2 mg of stannous chloride dihydrate, and 344 g (4 moles) of isovaleral was used further to give 216.0 g of isovaleral dimethallyl acetal (yield: 83.4%, based on methallyl alcohol).

Example 25

The general procedure of Example 8 was repeated except that 0.2 mg of titanium oxy acetylacetonate was used instead of 0.2 mg of stannous chloride dihydrate to give 23.4 g of isovaleral ethylene glycol acetal (yield: 90.2%).

This application is based on Japanese Patent Application 311,548/95, filed Nov. 6, 1995, and on Japanese Patent Application 325,003/95, filed Nov. 20, 1995, which are incorporated by reference herein in their entirety.

Obviously, numerous modifications and variations are possible in light of the above teachings. It is therefore to be understood that within the scope of the appended claims the present invention can be practiced otherwise than as specifically described herein.

What is claimed as new and is desired to be secured by Letters Patent of the United States is:

1. A process for producing an acetal represented by the following formula (4) or (5):

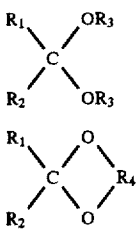

(4)

(5)

wherein $R_1$ and $R_2$ each independently represents a hydrogen atom or a monovalent hydrocarbon group with 1 to 20 carbon atoms which can have a substituent, or $R_1$ and $R_2$ are coupled together to form an alkylene group which can have an ethereal bond therein; $R_3$ represents a monovalent hydrocarbon group with 1 to 20 carbon atoms which can have a substituent; and $R_4$ represents an alkylene group which can have an ethereal bond therein, comprising reacting an aldehyde or a ketone represented by the following formula (1):

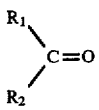

wherein $R_1$ and $R_2$ have the same meanings as defined above with an alcohol represented by the following formula (2) or (3):

      (2)

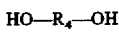      (3)

wherein $R_3$ and $R_4$ have the same meanings as defined above, in the presence of a catalyst selected from the group consisting of stannous chloride dihydrate, a titanium compound having acetylacetone as a ligand and a mixture of said catalyst.

2. The process for producing an acetal according to claim 1, wherein the titanium compound having acetylacetone as a ligand is at least one compound selected from the group consisting of titanium acetylacetonate, titanium oxy acetylacetonate and titanium oxy acetylacetonate polymer.

3. The process of claim 1, wherein $R_1$, $R_2$ and $R_3$ are the same or different and are an alkyl group, a cycloalkyl group, an alkenyl group, an alkynyl group, an aralkyl group or a cinnamyl group.

4. The process of claim 3, wherein the alkyl group is methyl, ethyl, propyl, n-butyl, t-butyl, isoamyl or octyl.

5. The process of claim 3, wherein the cycloalkyl group is cyclopentyl or cyclohexyl.

6. The process of claim 3, wherein the alkenyl group is allyl, methallyl, crotyl or phenyl.

7. The process of claim 3, wherein the alkynyl group is 2-propynyl.

8. The process of claim 1, wherein one or both of $R_1$ and $R_2$ are aryl groups.

9. The process of claim 8, wherein the aryl group is phenyl, tolyl, xylyl or naphthyl.

10. The process of claim 3, wherein the aralkyl group is benzyl or phenethyl.

11. The process of claim 1, wherein one or more of $R_1$, $R_2$ or $R_3$ are substituted.

12. The process of claim 11, wherein one or more of $R_1$, $R_2$ or $R_3$ are substituted with a halogen atom, carboxyl group, alkoxycarbonyl group, or alkoxy group.

13. The process of claim 1, wherein $R_1$ and $R_2$ together form an alkylene group containing an ethereal bond therein.

14. The process of claim 13, wherein $R_1$ and $R_2$ together form ethylene, propylene, tetramethylene, pentamethylene or a divalent group represented by one of the following formulas:

—CH$_2$—O—CH$_2$— or

—CH$_2$—CH$_2$—O—CH$_2$—CH$_2$—.

15. The process of claim 1, wherein the aldehyde is formaldehyde, acetaldehyde, propionaldehyde, butyraldehyde, isobutyraldehyde, isovaleral, hexanal, octanal, methacrolein, crotonaldehyde, senecioaldehyde, citral, citronellal, benzaldehyde or cinnamaldehyde.

16. The process of claim 1, wherein the ketone is methyl ethyl ketone, pinacolone, cyclohexanone, 2-octanone, mesityl oxide, 6-methyl-5-hepten-2-one, acetophenone or propiophenone.

17. The process of claim 1 wherein the alcohol is methanol, ethanol, propanol, butanol, allyl alcohol, methallyl alcohol, prenol, isoprenol, geraniol, nerol, benzyl alcohol, 2-phenylethanol, ethylene glycol, 1,2-propanediol, 1,4-butanediol or diethylene glycol.

18. The process of claim 17, wherein a hydroxyl group in the alcohol is at least 1 mole per mole of a carbonyl group in the aldehyde or ketone.

19. The process of claim 1, wherein the catalyst is stannous chloride dihydrate.

20. The process of claim 19, wherein the catalyst is used in a range of 0.1 ppm to 2% relative to the reaction mixture.

* * * * *